United States Patent [19]

Chuman et al.

[11] 4,317,836

[45] Mar. 2, 1982

[54] 4-6-DIMETHYL-7-KETO-NONAN-3-OL AND SEX ATTRACTANT COMPRISING THE SAME

[75] Inventors: Tatsuji Chuman; Masahiro Kono; Kunio Kato, all of Yokohama, Japan

[73] Assignee: The Japan Tobacco & Salt Public Corporation, Tokyo, Japan

[21] Appl. No.: 117,025

[22] Filed: Jan. 30, 1980

[30] Foreign Application Priority Data

Mar. 28, 1979 [JP] Japan .................................. 54-35518

[51] Int. Cl.³ ...................... C07C 49/17; A01N 35/02
[52] U.S. Cl. ...................................... 424/331; 424/84; 568/414
[58] Field of Search .................... 568/414; 424/84, 331

[56] References Cited

U.S. PATENT DOCUMENTS 3,910,897 10/1975 Chodnekar et al. ................. 568/414
3,927,207 12/1975 Francke et al. ...................... 424/84
3,936,424 2/1976 Demale ................................ 568/414

OTHER PUBLICATIONS

Chuman et al., Tet. Lett, 1979, #25, pp. 2361–2364 (1979).

Chuman et al., Chem. Abst., vol. 92, #41267k (1980).

*Primary Examiner*—Natalie Trousof
*Assistant Examiner*—James H. Reamer
*Attorney, Agent, or Firm*—Lilling & Greenspan

[57] ABSTRACT

A novel compound, 4,6-dimethyl-7-keto-nonan-3-ol is extracted from female imagoes of cigarette beetle. This novel compound is the sex pheromone of cigarette beetle and has sex attracting activity to male imagoes. A sex attracting composition comprises the novel compound and a solid carrier. The compound may be impregnated or adsorbed in the carrier.

6 Claims, No Drawings

4-6-DIMETHYL-7-KETO-NONAN-3-OL AND SEX ATTRACTANT COMPRISING THE SAME

BACKGROUND OF THE INVENTION

This invention relates to a novel compound 4,6-dimethyl-7-keto-nonan-3-ol and a sex attracting composition comprising the same as an active ingredient.

It is well known that insecticide spraying for the prevention or extermination of plant pests causes hygenically undesirable problems. There is a strong demand for the development of a new pest prevention technique to substitute for insecticide spraying, or a new technique capable of reducing the amount of insecticide used.

Research has been made on pest prevention by attracting insects for catching and killing them, or disturbing the communication between male and female insects using an insect sex pheromone.

In general, the pairing behavior of insects is controlled by an extremely small amount of an odorous substance secreted by the insect, usually the female insect. The female insect releases a volatile, odorous substance in the air. The male insect perceives this odor and moves on legs or wings toward the female insect which is the source of the odor. The male insect who finds the female insect sexually excites and mates therewith.

The odorous substance secreted by female insects is generally called sex pheromone or sex attractant and is a very important substance in the mating behavior of insects.

The sex pheromone may be applied to pest prevention by attracting male insects to a given place to catch and kill them, or by disturbing the normal mating behavior of male imagoes. Alternatively, a sex pheromone may be used to attract and collect insect pests in order to make a field survey on the hatching or growing of the insect pests. On the basis of the results of such periodic surveys, it is possible to judge whether insecticide spraying is needed or not and to select the effective amount of an insecticide, thereby reducing the quantity of the insecticide used as a whole.

SUMMARY OF THE INVENTION

Bearing the above-mentioned general knowledge in mind, the inventors have attempted to use a sex attractant in the prevention of cigarette beetle (*Lasioderma serricorne F.*) which is an insect pest feeding on cured tobacco leaves and which causes serious damage to the tobacco industry every year. The inventors have found a novel compound having a strong male attracting activity in the hexane extract of female imagoes, and have succeeded in isolating the compound.

An object of this invention is to provide a novel compound which is the sex pheromone of cigarette beetle.

This invention provides a compound, 4,6-dimethyl-7-ketononan-3-ol having the structure:

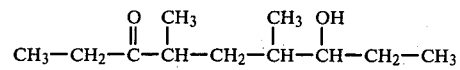

According to another aspect of this invention, there is provided a sex attracting composition which comprises 4,6-dimethyl-7-keto-nonan-3-ol as an active ingredient.

The instant compound according to this invention is a novel compound which is isolated for the first time from the natural world.

The instant compound may, for example, be extracted and identified in the following manner.

In a culture medium of cone powder in admixture with 0.8% by weight of EBIOS (trade mark, manufactured and sold by Tanabe Pharmaceutical Company, Japan), cigarette beetles were cultivated. Approximately 130,000 imagoes (4 to 6 day-old, male to female ratio=1:1) were immersed for 24 hours in about 2,000 ml of hexane for extraction. After filtration, the resulting extractant was evaporated in vacuum at a temperature of 30°–35° C., obtaining 5.0 g of a concentrate. The concentrate was mixed with 10 ml of pyridine and 10 ml of acetic anhydride, and the mixture was allowed to stand overnight so that acetylation took place, obtaining 5.5 g of an acetylated product.

The acetylated product was then fractionated by column chromatography using about a six times larger amount (32 g) of silicic acid (Malinkrodt Company, United States). Specifically, 100 ml of hexane, 100 ml of 98/2 hexane/ether mixture, and 100 ml of 95/5 hexane/ether mixture were sequentially passed through the column. Finally, 200 ml of 90/10 hexane/ether mixture was passed therethrough and the resulting elute was evaporated in vacuum at a temperature of 30°–35° C., obtaining 20 mg of a concentrate.

The concentrate was subjected to preparative gas chromatography using an FFAP column of 1 m × 3 mm diameter (Chromosorb AW with 5% coating, manufactured and sold by Johns-Manville Company, USA) equipped with a thermal conductive detector (TCD). Under analytical conditions the oven temperature was raised from 50° C. to 200° C. at a rate of 10° C./min. and He was fed as a carrier gas at a flow rate of 30 ml/min. a portion appearing at a peak Rt=7.0 was collected in a glass capillary tube connected to the outlet of the gas chromatograph using a cold bath. A pure compound which was an acetylated derivative of the instant compound weighed 1.5 mg.

The acetylated derivative of the instant compound which itself has no sex attracting activity, can readily be saponified into the corresponding alcohol form or the instant compound by adding a methanol solution containing 3% by weight of potassium hydroxide. The resulting compound has a strong attracting activity to male cigarette beetles, especially to non-mated males.

Since the instant compound is relatively unstable, it is generally isolated and stored in the stable acetylated form. The acetylated derivative of the instant compound was determined with infrared spectrum, mass analysis spectrum, and H- and $^{13}C$-nuclear magnetic resonance spectrum.

IR spectrum: 2970(s), 2930(s), 1735(s), 1715(s), 1460(m), 1370(m), 1240(s), 1100(m), 1018(m), 960(m) and 800(w) cm$^{-1}$. Letters s, m and w in the parentheses designate strong, medium and weak absorption intensities, respectively.

Mass analysis spectrum: M+ =41(37), 43(100), 55(30), 57(65), 69(40), 70(18), 83(21), 86(46), 99(8), 111(21), 127(3), 139(13), 157(11), 168(7), 185(2) and 228(0.1) m/e. Figures in the parenthese designate the intensities of signals.

Proton NMR spectrum 0.86(3H, t, J=7 Hz), 0.98(3H, d, J=6 Hz), 1.04(3H, t, J=7 Hz), 1.03(3H, d, J=7 Hz), 1.2—1.6(5H, m), 2.06(3H, s), 2.42(2H, s, J=7 Hz), 2.60(1H, m) and 4.76(1H, m) ppm. Proton number and splittings are designated in the parentheses.

$^{13}$C NMR spectrum 7.84(Q, —CH$_3$), 10.18(Q, —CH$_3$), 14.45(Q, —CH$_3$), 16.67(Q, —CH$_3$), 21.06(Q, —OCOCH$_3$), 24.22 (t, —CH$_2$—), 33.70

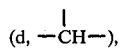

34.22(t, —CH$_2$—), 35.98(t, —CH$_2$—), 43,53

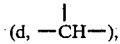

78,04

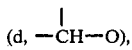

170.88(S, —O0COCH$_3$) 214.88

ppm. The splittings obtained by the off-resonance method and their attribution are shown in the parentheses.

The instant compound is a pale yellow viscous liquid at room temperature which is ready for use as such. In order for the instant compound to be effective for a longer period of time, it may be impregnated in a rubber plug or charged in a plastic capsule, for example. The instant compound may be adsorbed in a suitable carrier by suspending a particulate carrier in a solution of the instant compound in an organic solvent and evaporating the solvent at a low temperature, typically about 40° C. in vacuum. Examples of the preferred carriers include powdery or particulate synthetic resins and inorganic materials such as sand, diatomaceous earth and silica gel. The carrier may be used in an amount about 100 to 1000 times, particularly about 500 times larger by weight than the amount of the active compound used. The solvents may include hexane, benzene, ethyl ether, ethyl alcohol, methyl alcohol, etc.

The sex attractant according to this invention may be placed at a desired location to attract male imagoes of cigarette beetle thereto so that they may be caught and killed, thereby reducing the number of imagoes. The sex attractant may also be sprayed in the air at a relatively high concentration to prevent male imagoes from finding female imagoes to disturb mating of male and female imagoes, thereby suppressing the propagation thereof.

Attracting insecticides may be prepared by mixing the instant compound with any conventional insecticides. In addition to the above-described pest prevention, the instant compound or the attractant comprising the same may be used in a survey on the occurrence of cigarette beetle, or for determining the time and quantity of occurrence of the pest.

The efficacy of the sex attractant according to this invention will be more fully understood from the following examples.

EXAMPLE 1

The instant compound was dissolved in hexane in varying amounts shown in Table I to prepare test solutions. Using a syringe, 1 microliter of the test solution was applied to a paper filter of 1.5 cm×0.5 cm which had been folded twice. The compound used in this Example was extracted and isolated from female cigarette beetle imagoes as described in the foregoing.

Dishes with a cover plate having a diameter of 10 cm were prepared. Then non-mated 4 to 6 day-old male imagoes of cigarette beetles were introduced in each dish. The paper filters impregnated with 1 microliter of the above-prepared solutions were placed in the dishes, respectively. A paper filter impregnated with 1 microliter of hexane was used as a control. The results were shown in Table I. The value shown is an average of three tests for each sample.

TABLE I

| Sample No. | Instant compound (μg) | Number of males gathered on the filter impregnated with attractant | Number of males gathered on the filter impregnated with hexane only |
|---|---|---|---|
| 1 | 20 | 10 | 0 |
| 2 | 2 | 10 | 0 |
| 3 | 2 × 10$^{-1}$ | 10 | 0 |
| 4 | 2 × 10$^{-2}$ | 10 | 0 |
| 5 | 2 × 10$^{-3}$ | 10 | 0 |
| 6 | 2 × 10$^{-4}$ | 10 | 0 |
| 7 | 2 × 10$^{-5}$ | 7 | 0 |
| 8 | 1 × 10$^{-5}$ | 2 | 0 |

As seen from the results of Table I, the instant compound exhibits a strong attracting activity with respect to non-mated male cigarette beetles.

EXAMPLE 2

In a biological assay box of 2 m×2 m×2 m having net side surfaces, two plates having an adhesive applied thereto for trapping and of a size of 10 cm×10 cm were placed in a symmetrical fashion. A rubber plug having 100 μg of the instant compound applied was placed on one trapping plate and a control rubber plug having no agent applied was placed on the other trapping plate. About 4000 imagoes of cigarette beetle (male to female ratio 1/1) were introduced into the box, which was allowed to stand one day in the dark. The numbers of imagoes trapped on the respective plates were counted. The results are shown in Table II.

TABLE II

| | Number of imagoes trapped on | |
|---|---|---|
| Test No. | plate having sex pheromone-treated plug | control plate |
| 1 | 401 | 24 |
| 2 | 453 | 38 |
| 3 | 378 | 32 |

As seen from the results of Table II, the instant compound is highly effective to attract male cigarette beetles.

What is claimed is:

1. Pure 4,6-dimethyl-7-keto-nonan-3-ol having the structure:

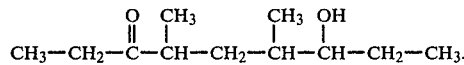

2. A sex attractant comprising a carrier and pure 4,6-dimethyl-7-keto-nonan-3-ol as an active ingredient.

3. A sex attractant according to claim 2 wherein the carrier is a particulate solid capable of adsorbing the active ingredient, and wherein 1 part by weight of the active ingredient is adsorbed in 100 to 1000 parts by weight of the carrier.

4. A sex attractant according to claim 3 wherein said carrier is selected from the group consisting of a synthetic resin, sand, diatomaceous earth or silica gel.

5. A sex attractant according to claim 3, wherein 1 part by weight of the active ingredient is adsorbed in 500 parts by weight of the active ingredient.

6. A sex attractant for cigarette beetles according to any of claims 2, 3, 4 or 5.

* * * * *